United States Patent
Dohmen et al.

(10) Patent No.: US 10,743,936 B2
(45) Date of Patent: Aug. 18, 2020

(54) METHOD AND APPARATUS FOR JUDGING IMPLANT ORIENTATION DATA

(71) Applicants: Smith & Nephew, Inc., Memphis, TN (US); Smith & Nephew Asia Pacific Pte. Limited, Singapore (SG); Smith & Nephew Orthopaedics AG, Zug (CH)

(72) Inventors: Lars Dohmen, Munich (DE); Mario Schubert, Poing (DE); Anna Wiedenmann, Feldkirchen (DE)

(73) Assignees: Smith & Nephew, Inc., Memphis, TN (US); Smith & Nephew Asia Pacific Pte. Limited, Singapore (SG); Smith & Nephew Orthopaedics AG, Zug (CH)

( * ) Notice: Subject to any disclaimer, the term of this patent is extended or adjusted under 35 U.S.C. 154(b) by 638 days.

(21) Appl. No.: 15/508,764

(22) PCT Filed: May 8, 2015

(86) PCT No.: PCT/EP2015/060195
§ 371 (c)(1),
(2) Date: Mar. 3, 2017

(87) PCT Pub. No.: WO2016/180438
PCT Pub. Date: Nov. 17, 2016

(65) Prior Publication Data
US 2018/0235702 A1    Aug. 23, 2018

(51) Int. Cl.
*A61B 34/10* (2016.01)
*A61B 34/20* (2016.01)
(Continued)

(52) U.S. Cl.
CPC .............. *A61B 34/10* (2016.02); *A61B 5/1118* (2013.01); *A61B 5/1122* (2013.01); *A61B 34/20* (2016.02);
(Continued)

(58) Field of Classification Search
CPC ........... A61B 34/10; A61B 34/20; A61B 5/11; A61B 5/1121; A61B 2034/102; A61B 5/4538; A61F 2/46
See application file for complete search history.

(56) References Cited

U.S. PATENT DOCUMENTS

| 5,995,738 A | 11/1999 | Digioia et al. |
| 2001/0008981 A1 | 7/2001 | Masini |

(Continued)

FOREIGN PATENT DOCUMENTS

| DE | 202010008404 U1 | 12/2010 |
| WO | 2012097873 A1 | 7/2012 |
| WO | 13117909 A1 | 8/2013 |

OTHER PUBLICATIONS

Turley, G.A., University of Warwick institutional repository: Graphical representation of range of motion in the assessment of total hip arthroplasty, Abstract, Mar. 2012, UK.
(Continued)

*Primary Examiner* — Patrick Fernandes
(74) *Attorney, Agent, or Firm* — Troutman Pepper

(57) ABSTRACT

A data processing method performed by a computer for judging implant orientation data representing an orientation of a first implant part relative to a first bone, the first implant part being part of an implant pair which further comprises a second implant part for a second bone, the implant pair being envisaged to be implanted in a patient.

23 Claims, 5 Drawing Sheets

Figure 1:
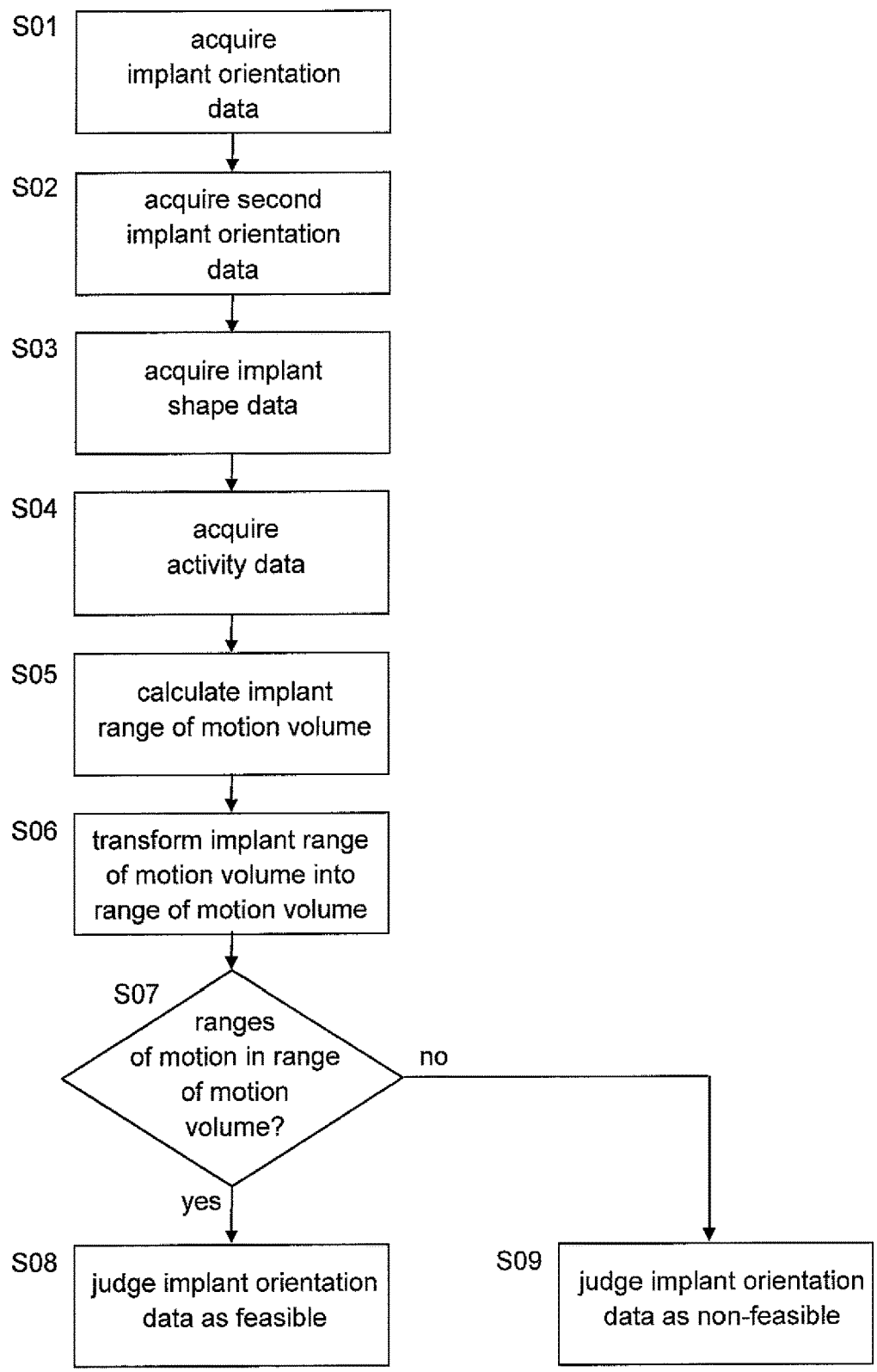

(51) Int. Cl.
*A61B 5/11* (2006.01)
*A61F 2/46* (2006.01)
*A61B 5/00* (2006.01)

(52) U.S. Cl.
CPC ........... *A61B 5/4571* (2013.01); *A61B 5/4595* (2013.01); *A61B 2034/102* (2016.02); *A61B 2034/104* (2016.02); *A61B 2034/2051* (2016.02); *A61B 2034/2057* (2016.02); *A61B 2034/2063* (2016.02); *A61F 2002/4633* (2013.01)

(56) References Cited

U.S. PATENT DOCUMENTS

| | | | |
|---|---|---|---|
| 2008/0287962 | A1 | 11/2008 | Dick et al. |
| 2008/0294265 | A1 | 11/2008 | Warkentine et al. |
| 2009/0164024 | A1 | 6/2009 | Rudan et al. |

OTHER PUBLICATIONS

Roach et al., "Normal Hip and Knee Active Range of Motion: The Relationship to Age", Article, Physical Therapy, vol. 71, No. 9, Sep. 1991 pp. 656-665, US.

DePuy Orthopaedics, Inc., "Pinnancle Hip Solutions, Polyethylene Surgical Technique", Brochure, pp. 1-44, Document No. 0612-83-512 2.5M, Jun. 2013, Warsaw, IN.

Zhou et al., "Motion performance and impingement risk of total hip arthroplasty with a simulation module", Journal, pp. 849-854, Zhejiang University—Science B: International Biomedicine & Biotechnology Journal, vol. 14. No. 9, Sep. 1, 2013, China.

Turley et al., "Establishing a range of motion boundary for total hip arthroplasty", Proceedings of the Institution of Mechanical Engineers. Journal of Engineering in Medicine. Part H., vol. 225, No. 8, Aug. 1, 2011, pp. 769-782, XP055242315, GB.

Moctezuma et al., "Assessment of the Hip Range of Motion Envelope in Total Hip Arthroplasty using a Graphical Interface", 56th. Annual Meeting of the Orthopaedic Research Society, Mar. 9, 2010, XP055242161. p. 1.

Seel, "Three-dimensional Planning and Virtual Radiographs in Revision Total Hip Arthroplasty for Instability", Clinical Orthopaedics and Related Research, Jan. 31, 2006, pp. 35-38, XP055242418.

Widmer, "Containment versus impingment: finding a comprise for cup placement in total hip arthroplasty", International Orthopaedics, Springer, vol. 31, No. 1, Jul. 28, 2007, pp. 29-33, XP019539149 Berlin, DE.

Widmer et al., "The impact of the CCD-angle on range of motion and cup positioning in total hip arthroplasty", Clinical Biomechanics, Butterworth Scientific Ltd., vol. 20, No. 7, Aug. 1, 2005, pp. 723-728, XP027795105, Guildford, GB.

Widmer et al, "Compliant positioning of total hip components for optimal range of motion", Journal of Orthopaedic Research, vol. 22, No. 4, Jul. 1, 2004 pp. 815-821, XP055242293, US.

Schulze et al. "Interactive simulation and comparative visualisation of the bone-determined range of motion of the human shoulder" Simulation and Visualisierung 2006, Jan. 1, 2006, pp. 275-287, XP009163497, SCS-Verlag Magdeburg, DE.

International Search Report for PCT/EP2015/060195 dated Jan. 25, 2016, EPO, NL.

Written Opinion of the International Searching Authority for PCT/EP2015/060195 dated Jan. 25, 2016, EPO, NL.

METHOD AND APPARATUS FOR JUDGING IMPLANT ORIENTATION DATA

RELATED APPLICATION DATA

This application is a national phase application of International Application No. PCT/EP2015/060195 filed May 8, 2015 published in the English language.

The present invention relates to a data processing method, performed by a computer, for judging implant orientation data representing an orientation of a first implant part relative to a first bone and to a corresponding computer program and system.

Implanting an artificial joint in a patient is a widely used medical task. The artificial joint is formed by an implant pair comprising a first implant part to be attached to a first bone which interacts with a second implant part to be attached to a second bone. The effect of the artificial joint strongly depends on whether or not the implant parts are suitably positioned on, in particular aligned or oriented with, the respective bones. A suitable functionality of the artificial joint, which is also referred to as implant joint, can typically not only be achieved for a single orientation between an implant part and a bone, but over a range of orientations. While the location of an implant part relative to the bone might have an influence on the functionality of the artificial joint, the present invention concentrates on the orientation of an implant part relative to a bone. In particular, this document relates to judging implant orientation data representing an orientation of a first implant part relative to a first bone, the first implant part being part of an implant pair which further comprises a second implant part for a second bone, the implant pair being envisaged to be implanted in a patient.

In this document, an implant part is a part of an artificial joint which is assigned to a bone. This means that an implant part might comprise one or more components which make up the implant part.

The method, the program and the system are defined by the appended independent claims. Advantages, advantageous features, advantageous embodiments and advantageous aspects of the present invention are disclosed in the following and contained in the subject-matter of the dependent claims. Different advantageous features can be combined in accordance with the invention wherever technically expedient and feasible. Specifically, a feature of one embodiment which has the same or a similar function to another feature of another embodiment can be exchanged with said other feature, and a feature of one embodiment which adds an additional function to another embodiment can in particular be added to said other embodiment.

According to the present invention, a data processing method performed by a computer for judging implant orientation data representing an orientation of a first implant part relative to a first bone, the first implant part being part of an implant pair which further comprises a second implant part for a second bone, the implant pair being envisaged to be implanted in a patient, comprises the steps of acquiring the implant orientation data and of acquiring the second implant orientation data representing the orientation of the second implant part relative to the second bone. Typically, the orientation of the second implant part relative to the second bone is given, and a particular orientation of the first implant part relative to the first bone is to be judged. The implant orientation data and/or the second implant orientation data is for example measured, assumed, calculated or received from a planning process.

The method further comprises the steps of acquiring implant shape data representing the shapes of the first and second implant parts and of acquiring activity data representing at least one desired activity of the patient to be possible after implanting the implant, wherein each desired activity has an associated range of motion between the first bone and the second bone. The shapes of the implant parts limit the interaction of the two implant parts, and in particular limit the possible joint orientations of the artificial joint. A desired activity is an activity the patient shall be able to perform with the artificial joint. An activity is for example an activity out of a predefined set of so-called activities of daily living (ADL), which can be considered as an atlas of activities.

Still further, the method comprises the step of calculating a range of motion volume, which represents possible orientations between the first bone and the second bone over three rotational axes, from the implant orientation data, the second implant orientation data and the implant shape data. An implant range of motion volume, which represents possible orientations between the first implant part and the second implant part, is calculated from the implant shape data. A possible orientation is an orientation which is attainable depending on at least the geometry of the implant parts. The implant range of motion volume is then for example transformed into the range of motion volume by use of the implant orientation data and the second implant orientation data.

In this context, the term "volume" does not refer to a spatial volume, but to a part of a three-dimensional space which is spanned by the three axes of rotation. It is thus rather a volume of parameter values. However, the range of motion volume is not limited to three dimensions. It can also be two-dimensional, and thus a range of motion area, or one-dimensional, and thus a range of motion band. Implementing the present invention in two dimensions or one dimension only reduces the computational complexity and might be sufficient for some medical procedures.

The method further involves the step of judging the implant orientation data to be feasible if the ranges of motion of all desired activities lie within the range of motion volume. In other words, the range of motion volume describes the mobility of the artificial joint in terms of attainable relative orientations between the two bones and it is determined whether or not this mobility includes the required relative orientations between the two bones for all desired activities.

For the sake of brevity, this document also uses the expressions "orientation" or "orientation of the first/second implant part" as a short form of "orientation of the first/second implant part relative to the first/second bone".

An orientation between two bones or between two implant parts is typically defined by three rotations in three distinct, preferably orthogonal, rotational dimensions defined by corresponding axes of rotation. It is thus a point in a three-dimensional orientation space which is spanned by the axes of rotation. In the medical field, the axes of rotation are typically axes which are anatomically meaningful. The axes are for example the axes of flexion-extension rotation, adduction-abduction rotation and internal-external rotation.

In this case, a range of motion associated with a desired activity is for example defined by a required range of the flexion-extension rotation, a required range of the adduction-abduction rotation and a required range of the internal-external rotation. A desired activity can be performed if the orientation of the first implant relative to the first bone allows the artificial joint to assume joint orientations which enable those three ranges of rotational movement.

An orientation of an implant part relative to a bone typically also is a point in a three-dimensional orientation space which is spanned by three axes of rotation. However, those axes of rotation are for example defined with respect to the bone. It shall be noted that the orientation space can also be two-dimensional or one-dimensional, depending on the type of implant.

In one embodiment, the method further comprises the step of calculating a zero joint orientation of an implant joint formed by the first and second implant parts, in which the first and second bone are in a neutral position relative to each other, from the implant orientation data and the second implant orientation data. So the implant parts are in the zero joint orientation if the two bones are in their neutral position.

The neutral position between the first and second bones is a known position in the field of medicine and depends on the type of joint. In the hip joint as an example, the neutral position is the position in which the mechanical axis of the femur lies in a sagittal plane, for instance parallel to the midsagittal plane, and the mechanical axis and posterior condylar line of the femur describe a plane which is parallel to the frontal plane of the pelvis. The posterior condylar line connects the most posterior and distal femoral points. It might, however, not be possible to acquire or sample those points, for example during surgery. In this case, an option is to acquire the ankle epicondyle *piriformis* (AEP) plane defined by a *piriformis* point (the proximal point of the femur shaft axis), the center of the epicondyle axis and an ankle point of the flexed leg. A direction orthogonal to this AEP plane corresponds to the direction of the posterior condylar axis and thus forms, together with the mechanical axis, a plane which is parallel to the frontal plane of the pelvis in the neutral position.

The neutral position between two bones typically is the origin relative to which a range of motion is defined. This neutral position is achieved for a particular joint orientation of the implant joint which depends on how the implant parts are oriented relative to their respective bones, which is defined by the implant orientation data regarding the first implant part and the second implant orientation data regarding the second implant part.

In this embodiment, the method further involves the step of calculating an implant range of motion volume, which represents possible orientations between the first implant part and the second implant part relative to the zero joint orientation over the same three rotational axes as the range of motion volume, from the implant shape data. As explained above, the possible joint orientations depend at least on the shape of the implant parts, but could also be limited by other factors.

The method in this embodiment then further involves using the implant range of motion volume as the range of motion volume. With the neutral position and the zero joint orientation corresponding to the same relative orientation between the two bones, a deflection of the two implant parts relative to the zero joint orientation means the same deflection of the two bones relative to their neutral position. The range of motion volume therefore equals the implant range of motion volume.

In the method according to the first variant described so far, a comparison is made between a range of motion volume and ranges of motion associated with desired activities, which are both defined with respect to the bones. It is, however, equivalent to make a comparison between a range of motion volume and ranges of motion corresponding to the desired activities which are both defined with respect to the implant parts. A method according to a second variant following this approach is described next.

The method for judging implant orientation data representing an orientation of a first implant part relative to a first bone, the first implant part being part of an implant pair which further comprises a second implant part for a second bone, the implant pair being envisaged to be implanted in a patient according this variant, includes the steps of acquiring the implant orientation data, the second implant orientation data, the implant shape data and the activity data as described above.

The method further involves the step of transforming the ranges of motion associated with the desired activities into implant ranges of motion, which define corresponding ranges of motion between the first and second implant parts, by use of the implant position data and the second implant position data. The ranges of motion corresponding to the desired activities are thus transferred into the "implant world".

The method still further involves the step of calculating an implant range of motion volume, which represents possible orientations between the first implant part and the second implant part over three rotational axes, from the implant shape data. This step is the same as described above.

The method finally involves the step of judging the implant position data to be feasible if the implant ranges of motion corresponding to all desired activities lie within the implant range of motion volume. This step is similar to the judging step described above, but happens in the "implant world".

The methods according to the two variants therefore implement the same technical idea of judging whether or not given ranges of motion lie within an attainable range of motion volume, and differ only in the reference system in which the judgement is made.

In one embodiment of the second variant, the method further comprises the step of calculating a zero joint orientation of an implant joint formed by the first and second implant parts, in which the first and second bone are in a neutral position relative to each other, from the implant orientation data and the second implant orientation data. The implant range of motion volume is then calculated relative to the zero joint orientation. This is in analogy to the embodiment of the first variant described above, except for that the implant range of motion volume is not used as the range of motion volume.

The following disclosure is common to both variants except for embodiments in which a distinction is explicitly stated.

The implant does for example form a ball-and-socket joint, which is also referred to as ball joint. Typical ball-and-socket joints are the hip joint between the femur and the acetabulum of the pelvis or the shoulder joint formed between the humerus and the glenoid cavity of the shoulder blade. The implant pair is therefore suitable for replacing the hip joint or the shoulder joint.

The shapes of the first and second implant parts depend on the several factors, such as the type of joint to be replaced, the particulars (like gender or size) of the patient and the model of the implant parts. The implant shape data is for example acquired from a database in which the shapes of a plurality of first and second implant parts are stored.

As described above, each desired activity has an associated range of motion between the first bone and the second bone. A range of motion does for example define orientations between the first bone and the second bone which are required in order to perform the corresponding activity. A range of motion may be defined by the maximum movement, that is deflection, between the two bones during the activity, or by a plurality of orientations between the first bone and the second bone during the activity.

In one embodiment, the implant orientation data represents the orientation of the first implant part relative to the first bone in two rotational dimensions. This is particularly advantageous if the implant pair forms a ball-and-socket joint, in which the first implant part exhibits a rotational symmetry. It is then only necessary to consider the orientation in two rotational dimensions. Those two rotational dimensions for example correspond to the inclination and the anteversion of the first implant part.

In one embodiment, the range of motion volume is displayed on a display unit. This allows a user to analyze the range of motion volume. If the range of motion volume is three-dimensional, this embodiment for example involves displaying a sectional view of the range of motion volume.

In one embodiment, the range(s) of motion corresponding to one or more desired activities are displayed together with the range of motion volume. This allows a user to immediately recognize whether or not a desired activity is possible or in how far the range of motion associated with a particular desired activity lies within the range of motion volume. If the range of motion volume is three-dimensional and a sectional view of the range of motion volume is displayed, this for example involves displaying a sectional view of the range of motion, preferably regarding the same sectional plane as the range of motion volume.

In one embodiment, calculating the implant range of motion volume involves finding possible orientations between the two implant parts in which they do not impinge. A possible orientation thus is a reachable or attainable orientation between the two implant parts. Possible orientations lie within the implant range of motion volume, while an orientation in which the implant parts impinge lie outside the implant range of motion volume. The implant range of motion volume, and thus the range of motion volume, typically is a closed and continuous volume.

Whether or not the implant parts impinge is for example determined by a collision detection of 3D models of the first implant part and the second implant part. The 3D models for example are the implant shape data or are derived from the implant shape data. In one implementation, a particular relative position between the two 3D models is assumed, wherein the relative location between the 3D models is predetermined and the orientation between the two 3D models is iterated through a set of trial orientations. It is then determined whether or not the two 3D models intersect each other for a particular trial orientation. If they intersect each other, the two implant parts impinge for a particular trial orientation, and if they do not intersect each other, the implant parts do not impinge.

The trial orientations form a grid of discrete trial orientations in the orientation space. In one implementation, a trial orientation for which the implant parts do not impinge which has at least one neighboring trial orientation for which the implant parts do impinge is assumed as a trial orientation which forms the boundary of the implant range of motion volume. In this manner, a closed implant range of motion volume is obtained, and all orientations within this volume are assumed to be possible orientations, even if they were not trial orientations.

It shall be noted that more sophisticated approaches for collision detection can be applied, for example approaches which allow a particular translational shift between the two 3D models depending on the joint orientation and/or which incorporate additional information such as ligaments of the joint or bone structures. The range of motion of an artificial joint is in some cases not only limited by the shape of the implant parts, but is further limited by bones, in particular the bones the implant parts are attached to. In those cases, an implant part and a bone or two bones collide before the implant parts collide. This can be considered in the collision detection by also modeling the bones, for example as a part of a 3D model.

In one implementation, whether or not the implant parts impinge is determined by an analytical analysis of the implant shape data instead of by a collision detection using 3D models. As an alternative, the boundary of the implant range of motion volume is directly calculated by an analysis of the implant shape data. Like in the embodiment using collision detection of 3D models, the analytical analysis might also consider the mentioned additional information.

In one embodiment, each desired activity is associated with a set of one or more relative orientations between the first and the second bone. A range of motion corresponding to a desired activity lies within a range of motion volume if the range of motion volume comprises all relative orientations in the set. In the "implant world" variant, the one or more relative orientations are transformed into implant relative orientations by use of the implant orientation data and the second implant orientation data and it is determined whether or not the implant relative orientations lie within the implant range of motion volume. If there is only one relative orientation in the set, this relative orientation typically is the most extreme relative orientation between the bones. If there are two or more relative orientations, they typically resemble the trajectory of the two bones during the corresponding activity.

If a range of motion of a desired activity is defined by a set of one or more relative orientations between the first bone and the second bone, which are typically given relative to the neutral position between the two bones, it is tested whether or not the implant joint can reach a corresponding relative orientation between the first implant part and the second implant part relative to the zero joint orientation.

In one embodiment, the implant orientation data is obtained by tracking the first implant part, which means tracking the orientation of the first implant part relative to the first bone. Tracking the orientation of the first implant part is preferably performed using a medical tracking or navigation system which is able to determine the relative position between two objects, such as the first implant part and the first bone. Tracking can be performed as an accompanying step during an actual surgery in which the first implant part is to be attached to the first bone or as an accompanying task during a mock surgery which is performed on a dummy patient for training purposes.

In one embodiment, the method further comprises the step of outputting guidance information which indicates how the orientation of the first implant part relative to the first bone has to be changed, compared to the orientation as it is tracked, such that all desired activities are possible, which means that the (implant) ranges of motion of all desired activities lie within the (implant) range of motion volume. This allows guiding a user who handles the first implant part to a suitable orientation of the first implant part.

In one embodiment, the implant orientation data is virtual implant orientation data during an implant planning process. In a planning process, a planned orientation is determined for the patient to be treated. The planned orientation is for example an optimized orientation which depends on the characteristics of the patient. The planned orientation can then be judged.

In one embodiment, the method of the first variant further includes the step of determining the desired activities whose associated ranges of motion do not lie in the range of motion volume. The method according to the second variant further comprises the steps of determining the desired activities whose associated implant ranges of motion do not lie in the implant range of motion volume. In this embodiment, the desired activities which cannot be performed or which cannot be performed without limitations are identified. It is then possible to indicate those desired activities to a user. The user can then for example decide whether or not the implant orientation data is tolerable even though it does not allow all desired activities.

In one embodiment, the desired activities are prioritized. In the first variant of the method, the implant orientation data is judged to be feasible if the ranges of motion of a predetermined number of desired activities with the highest priority lie within the range of motion volume. In the method according to the second variant, the implant position data is judged to be feasible if the implant ranges of motion of a predetermined number of desired activities with the highest priority lie within the implant range of motion volume. In this embodiment, a particular orientation of the first implant part relative to the first bone is considered feasible if it allows a predetermined number of most important desired activities, even though it does not allow all desired activities.

The priorities are for example predefined in the atlas of activities of daily living or are individually assigned by a user.

The present invention further relates to a program which, when running on a computer, causes the computer to perform the method steps of the method described above and/or a program storage medium on which the program is stored, in particular in a non-transitory form.

The present invention further relates to a medical planning system for determining implant orientation data representing a range of functional orientations of a first implant part relative to a first bone, the first implant part being part of an implant pair which further comprises a second implant part for a second bone and to be implanted in a patient, comprising a computer on which the program described above is stored and/or run.

The method in accordance with the invention is for example a data processing method. The data processing method is preferably performed using technical means, for example a computer. The data processing method is preferably constituted to be executed by or on a computer and for example is executed by or on the computer. For example, all the steps or merely some of the steps (i.e. less than the total number of steps) of the method in accordance with the invention can be executed by a computer. An embodiment of the data processing method is a use of the computer for performing the data processing method. The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. An embodiment is directed to the use of such a substance or composition in the data processing method. The calculating steps described are for example performed by a computer.

Determining steps or calculating steps are for example steps of determining data within the framework of the technical data processing method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

The expression "acquiring data" for example encompasses (within the framework of a data processing method) the scenario in which the data are determined by the data processing method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the data processing method or program, for example from another program, a previous method step or a data storage medium, for example for further processing by the data processing method or program. The expression "acquiring data" can therefore also for example mean waiting to receive data and/or receiving the data. The received data can for example be inputted via an interface. The expression "acquiring data" can also mean that the data processing method or program performs steps in order to (actively) receive or retrieve the data from a data source, for instance a data storage medium (such as for example a ROM, RAM, database, hard drive, etc.), or via the interface (for instance, from another computer or a network). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The method in accordance with the invention is preferably at least partly executed by a computer, i.e. all the steps or merely some of the steps (i.e. less than the total number of steps) of the method in accordance with the invention can be executed by a computer.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

This invention can be part of a next generation of image-based or image-free hip software. The most advantage of this invention is the prediction of a postoperative range of motion and judgement of implant position to be functional or not functional based on desired activities or desired range-of-motion values, respectively.

Figure 2:
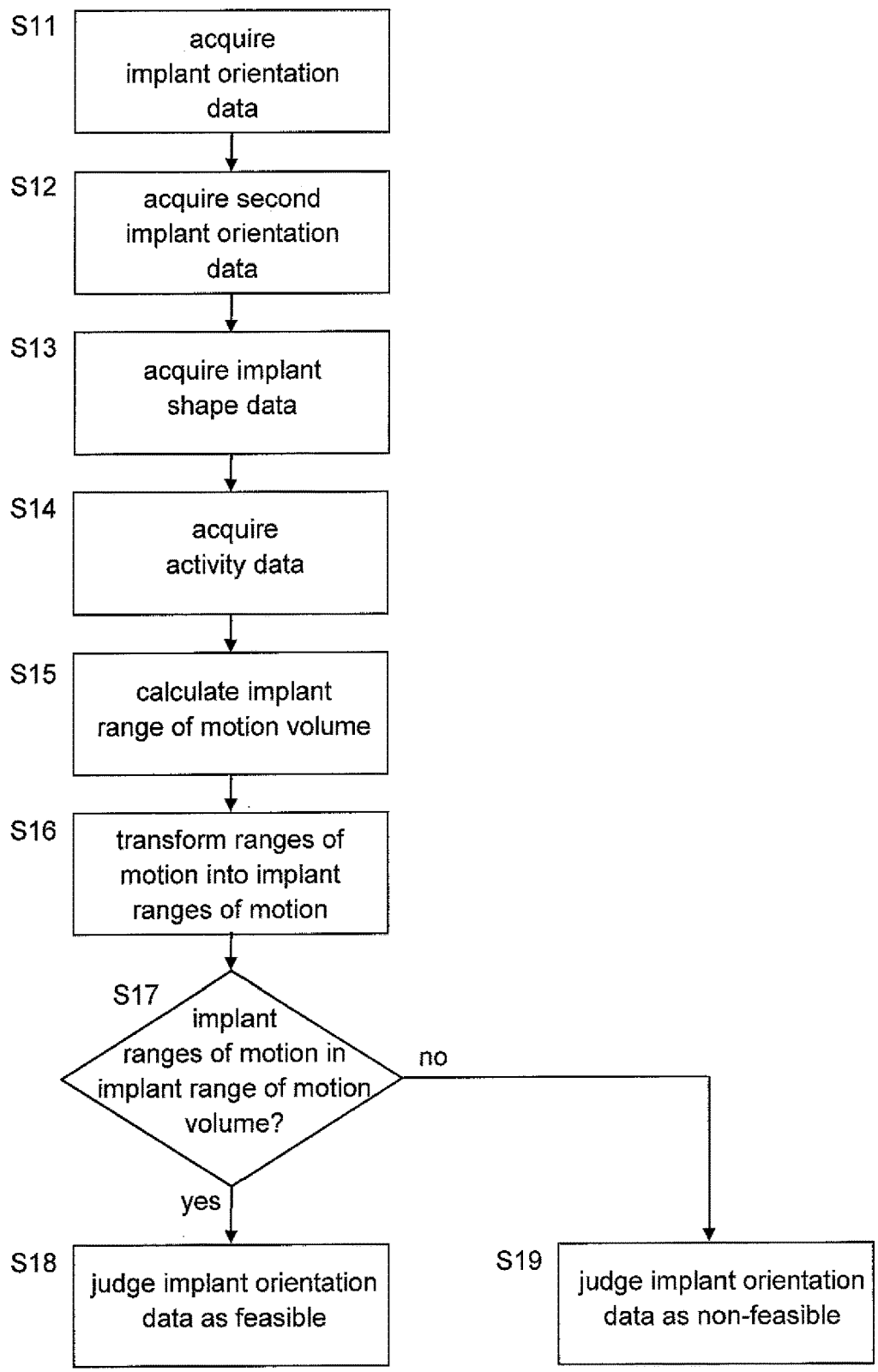
Figure 3:
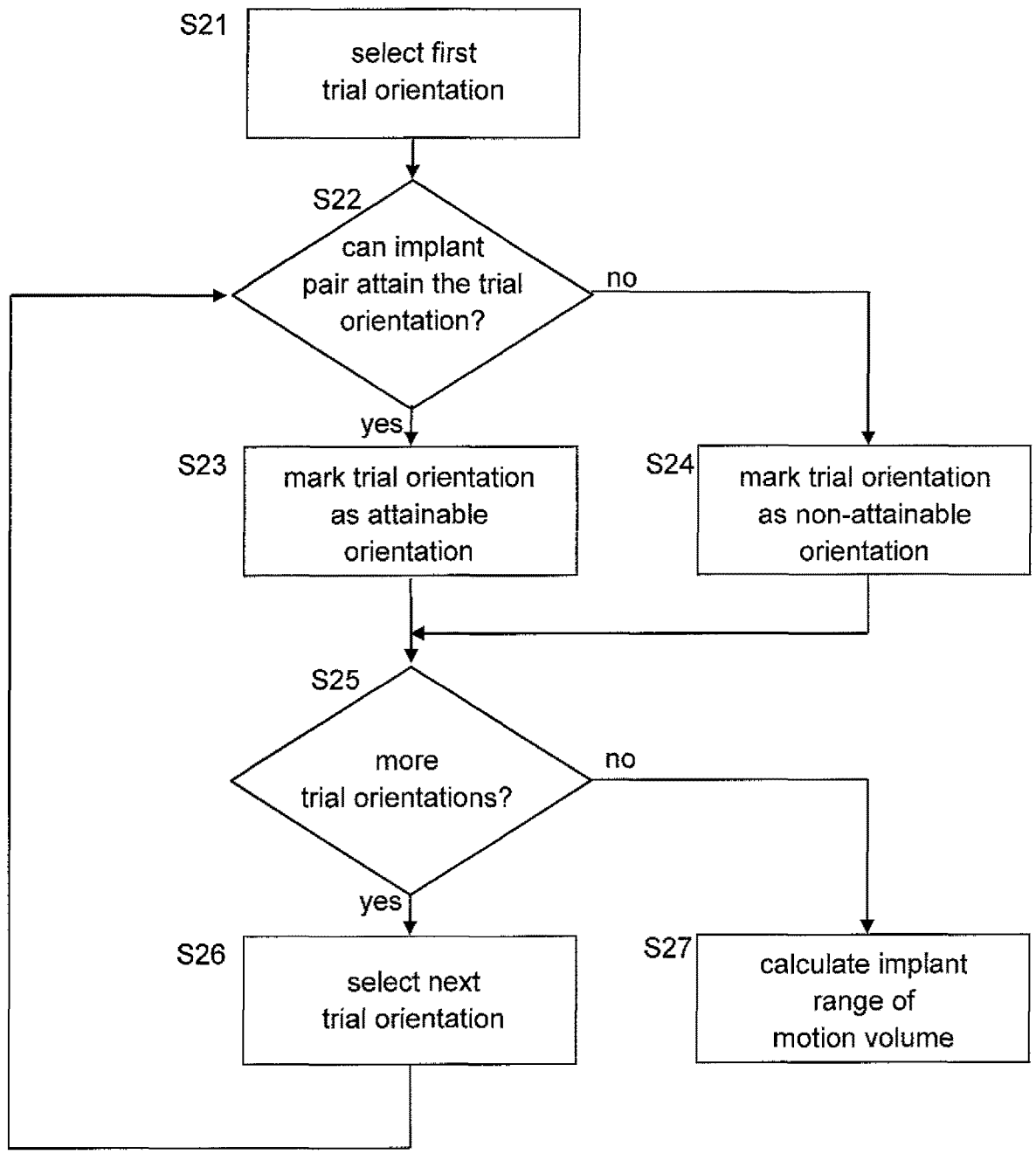
Figure 4:
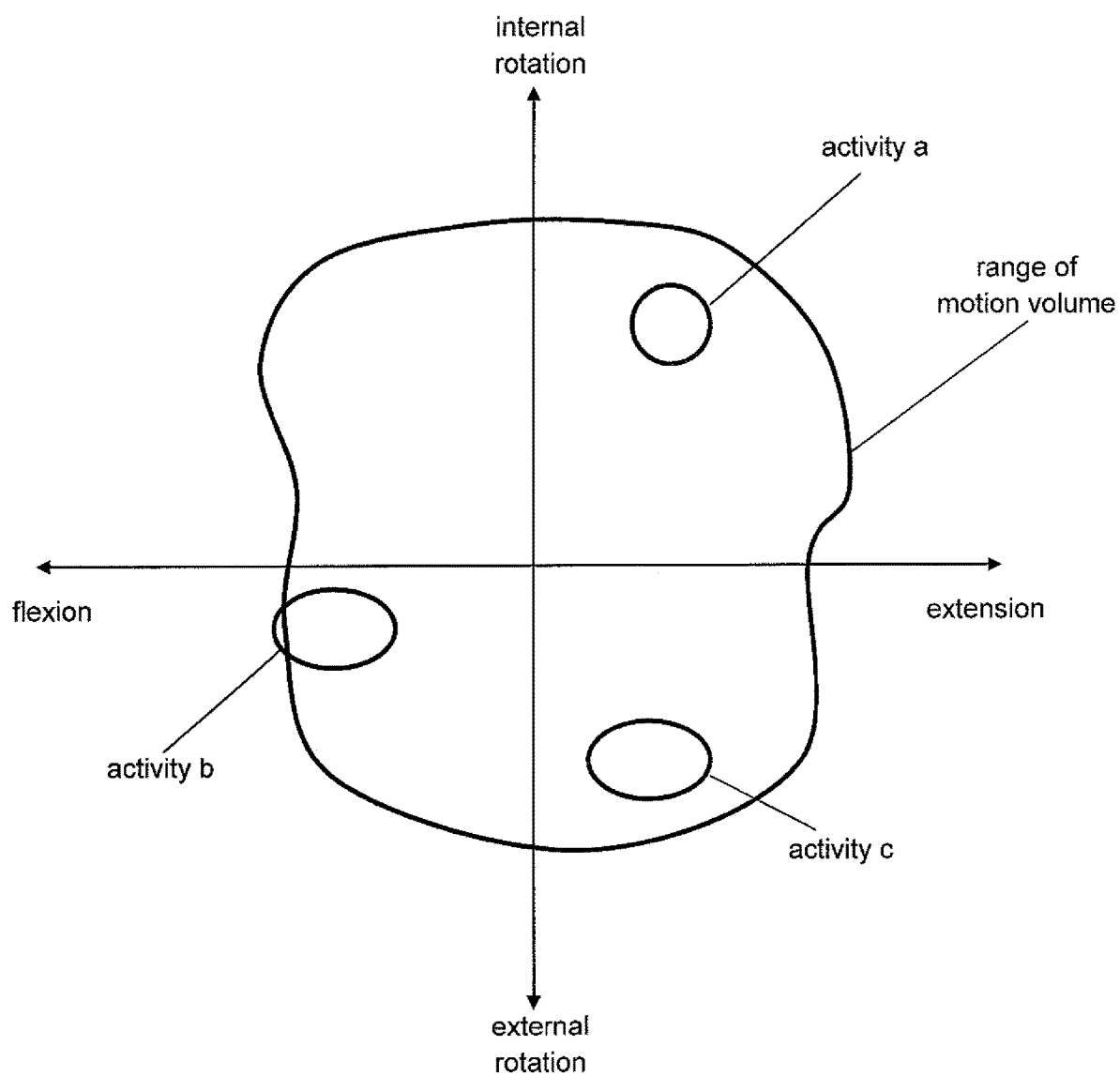
Figure 5:
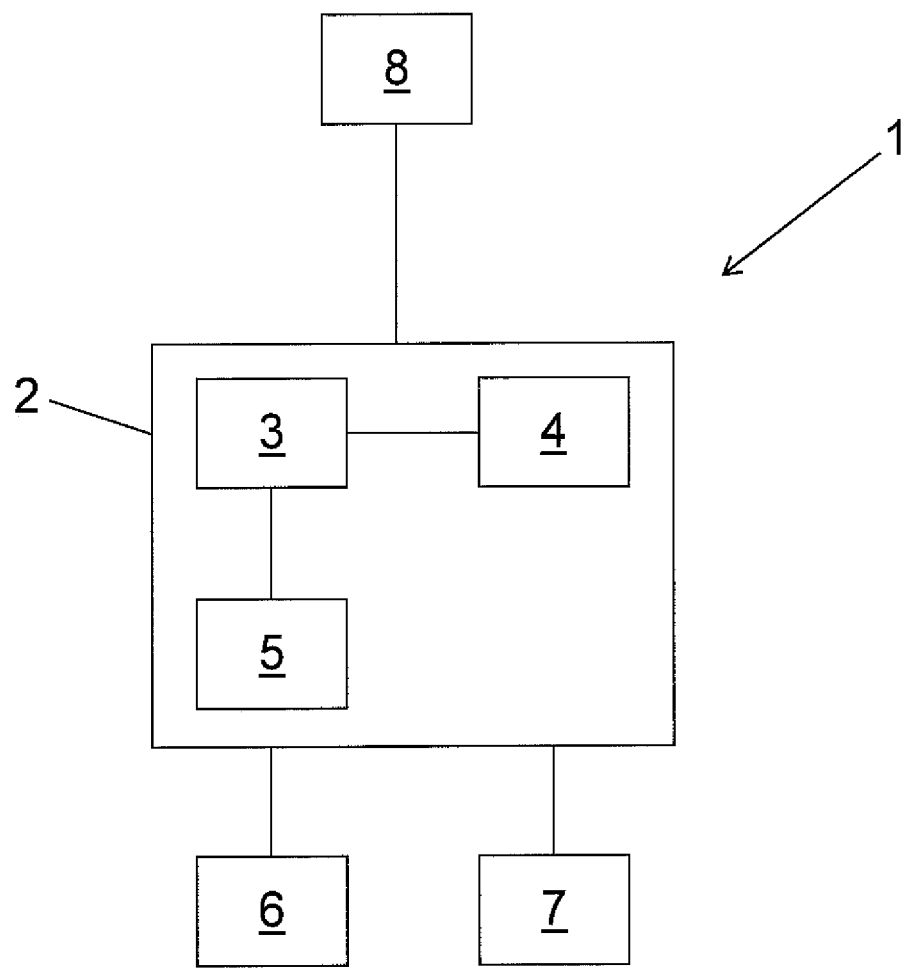

In the following, the invention is described with reference to the enclosed figures which represent preferred embodiments of the invention. The scope of the invention is not however limited to the specific features disclosed in the figures, which show:

FIG. 1 a flowchart of a first method for judging implant orientation data,

FIG. 2 a flowchart of a second method for judging implant orientation data,

FIG. 3 details of step S05 of FIG. 1 and step S15 of FIG. 2,

FIG. 4 a representation of a range of motion volume and ranges of motion of three activities and FIG. 5 a system for performing the method.

FIG. 1 shows a flow diagram of a first method for judging implant orientation data representing an orientation of a first implant part relative to a first bone. The first implant part and a second implant part together form an implant pair which forms an implant joint, which is also referred to as artificial joint. In an exemplary embodiment, the first bone is a pelvis and the second bone is a femur. In this case, an orientation of the first implant part relative to the pelvis is defined by an anteversion angle and an inclination angle. Those two angles span a two-dimensional implant orientation space.

An aspect of the present invention is to obtain a set of one or more desired activities of a patient who will receive the artificial joint and to judge whether or not the orientation of the first implant part will allow all desired activities. It shall be noted that the expression "orientation of an implant part" actually means "orientation of an implant part relative to a bone".

The present invention aims at judging the implant orientation data for the first implant part, assuming that the orientation of the second implant part relative to the second bone is already set. Step S01 therefore involves acquiring the implant orientation data to be judged and step S02 involves acquiring second implant orientation data representing the orientation of the second implant part relative to the second bone.

Step S03 involves acquiring implant shape data representing the shapes of the first implant part and the second implant part. The method according to the present invention is performed for a particular implant pair, the parts of which exhibit a particular shape, which can include the size of the implant parts. The implant shape data represents the three-dimensional geometry of the two implant parts. The shapes of the implant parts limit the interaction between the implant parts, and therefore the range of motion of the implant joint. The range of motion of the implant joint represents the relative orientations between the two implant parts which can be attained by the implant joint.

Step S04 involves acquiring activity data representing at least one desired activity of the patient to be possible after implanting the implant. The desired activities are for example selected from an atlas of activities of daily living (ADL), which is a predetermined list of activities such as basic activities like different hygiene activities, dressing, self-feeding or mobility, and instrumental activities such as housework, shopping or using objects. For example, one or more desired activities are selected from the atlas of activities of daily living.

Each desired activity has an associated range of motion between the first bone and the second bone. Such a range of motion describes the relative orientations between the first and second bone which are required in order to perform the corresponding activity. A range of motion or a relative orientation is typically defined with respect to a neutral position between the first and second bone.

Step S05 involves calculating an implant range of motion volume. The implant range of motion volume is a three-dimensional implant joint orientation space spanned by three linearly independent axes. Those axes are, in the present embodiment, the rotational axes of the flexion-extension rotation, the adduction-abduction rotation and the internal-external rotation. The implant range of motion volume is a part of the implant joint orientation space which defines relative orientations between the two implant parts which can be attained by the artificial joint.

The origin of the implant joint orientation space preferably is a zero joint orientation which corresponds to the neutral position between the two bones. The zero joint orientation is calculated from the implant orientation data and the second implant orientation data and is the orientation between the two implant parts which the artificial joint assumes if the two bones are in their neutral position. However, any other origin of the implant joint orientation space can be defined.

Step S06 involves transforming the implant range of motion volume into a range of motion volume which represents possible orientations between the first bone and the second bone.

The range of motion volume is, in analogy to the implant range of motion volume, a part of a bone orientation space which is spanned by three orthogonal axes, which preferably are the same axes as those which span the implant joint orientation space. If, in addition, the zero joint orientation corresponds to the neutral position between the two bones as described above, then the range of motion volume is the same as the implant range of motion volume. Step S06 therefore is also a step of calculating the range of motion volume.

Step S07 involves determining whether or not the ranges of motion associated with the desired activities lie within the range of motion volume. If this is the case (yes in step S07), it is judged in step S08 that the implant orientation data is feasible, which means that all desired activities could be performed if the first implant part was attached to the first bone with the orientation as represented by the implant orientation data.

If not all ranges of motion associated with the desired activities lie within the range of motion (no in step S07), it is judged in step S09 that the implant position data is not feasible.

FIG. 2 shows a flow diagram of a method according to a second embodiment of the present invention. This embodiment is similar to the one described with reference to FIG. 1. In particular, steps S11, S12, S13, S14 and S15 are the same as the steps S01, S02, S03, S04 and S05, respectively, described with reference to FIG. 1.

Step S16 involves transforming the ranges of motion associated with the desired activities into implant ranges of motion. This transformation can be calculated based on the implant orientation data and the second implant orientation data. In the case described in the first embodiment, in which a zero joint orientation corresponding to a neutral position of the two bones is calculated and the bone orientation space and the implant joint orientation space are spanned by the same rotational axes, the implant ranges of motion are the same as the ranges of motion associated with the desired activities.

Step S17 involves determining whether or not all implant ranges of motion lie in the implant range of motion volume. If this is the case (yes in step S17), the method proceeds to step S18 in which it is judged that the implant orientation data is feasible. If not all of the implant ranges of motion lie within the implant range of motion volume (no in step S17), it is judged in step S19 that the implant orientation data is not feasible.

FIG. 3 is a flow diagram which explains details of the step of calculating an implant range of motion volume, that is of step S05 in FIG. 1 and step S15 in FIG. 2.

In the present embodiment, an implant range of motion volume is calculated by testing a plurality of trial orientations for whether or not they can be attained by the artificial joint. In other words, the implant orientation space is sampled by a plurality of trial orientations. Due to the nature of an artificial joint, it can be assumed that the implant range of motion volume is limited by a closed boundary and all orientations within the closed boundary are attainable relative orientations between the two implant parts.

Step S21 involves selecting a first trial orientation.

Step S22 involves determining whether or not the two implant parts can attain the trial orientation. If this is the case (yes in step S22), the selected trial orientation is marked as an attainable orientation in step S23. If this is not the case (no in step S22), the selected trial orientation is marked as a non-attainable orientation in step S24.

The method then proceeds to step S25 in which it is determined whether or not there are more trial orientations to test. If this is the case (yes in step S25), the next trial orientation is selected in step S26 and the method returns to step S22. If this is not the case (no in step S25), the method proceeds to step S27.

In step S27, the implant range of motion volume is calculated based on the classification of the trial orientations into attainable and non-attainable orientations. In one implementation, step S27 involves to determine all trial orientations which are attainable orientations and which have at least one neighbouring trial orientation which is a non-attainable orientation. Those trial orientations then form the boundary of the implant range of motion volume.

Any suitable approach for iterating through and/or defining the trial orientations can be implemented, preferably an approach which optimizes the computational efficiency. It is further possible to define additional trial orientations to be tested between the attainable and non-attainable trial orientation in order to refine the range of motion volume.

Whether or not a trial orientation is attainable as determined in step S22 depends at least on the implant shape data. The determination may implement a collision detection approach which uses 3D models of the implant parts. If, for a particular trial orientation, the 3D models of the first and second implant part do not collide or intersect with each other, then the implant parts can reach said trial orientation.

Instead of implementing a collision detection based on 3D models, an analytical approach can be implemented which calculates an analytical description of the boundary of the implant range of motion volume.

Determining whether or not the implant joint can attain the trial orientation between the implant parts might consider additional information, such as ligaments of the joint or the shape of a bone.

FIG. 4 illustrates a sectional view or a slice of an exemplary range of motion volume, wherein the sectional plane is defined by the axes of internal-external rotation and flexion-extension rotation and the sectional view corresponds to a particular angle of the adduction-abduction rotation. It further shows a corresponding sectional view of three ranges of motion associated with three activities.

As can be seen from FIG. 4, the ranges of motion associated with the activities a and c lie within the range of motion volume, which means that those activities could be performed with an artificial joint having the first implant part attached to the first bone according to the tested implant orientation data. However, the range of motion corresponding to activity b does not lie within the range of motion volume, such that activity b cannot be performed without limitations. If only one or more of the activities a and c are desired activities, then the implant orientation data is judged to be feasible. If activity b is a desired activity, then the implant orientation data is judged to be not feasible. However, due to most of the range of motion associated with activity b lying within the range of motion volume, a user can decide that the implant orientation data might be acceptable anyway.

FIG. 5 shows a system 1 for judging implant orientation data as explained above. The system 1 comprises a computer 2 including a central processing unit 3, a memory unit 4 and an interface 5. The computer 2 is connected to an input unit 6, such as a mouse, a keyboard or a touch-sensitive surface, and an output unit 7 such as a display, a speaker or a tactile sensation generating unit. The input unit 6 is for example used to identify the particular implant pair for which the method is to be performed. The computer is further connected to an actual orientation determining unit 8. The computer 2 is connected to the units 6, 7 and 8 via the interface 5. The memory unit 4 stores working data, such as the implant orientation data, the second implant orientation data, the implant shape data and the activity data, and program code which instructs the central processing unit 3 to perform the method as explained above.

The actual orientation determining unit 8 can be a tracking unit which tracks a marker device attached to the first implant part or to an instrument to which the first implant part is attached. The tracking unit can for example be a stereoscopic camera or a transmitter or a receiver for electromagnetic radiation in an EM tracking system. However, the actual orientation determining unit might be a planning unit which plans the orientation between the first implant part and the first bone. The planning unit might be a software module which is executed on the computer 2.

The range of motion volume or the implant range of motion volume can be calculated based on the implant orientation data as obtained by tracking the first implant part relative to the first bone. Preferably, this calculation is performed continuously to continuously judge the actual orientation of the first implant part. The continuously calculated (implant) range of motion volume can be continuously displayed on the output unit 7, optionally together with the (implant) range(s) of motion associated with one or more desired activities.

The invention claimed is:

1. A data processing method performed by a computer for judging implant orientation data representing an orientation of a first implant part relative to a first bone, the first implant part being part of an implant pair which further comprises a second implant part for a second bone, the implant pair configured to be implanted in a patient, comprising the steps of:
   acquiring the implant orientation data;
   acquiring second implant orientation data representing an orientation of the second implant part relative to the second bone;
   acquiring implant shape data representing a shape of the first implant part and a shape of the second implant part;
   acquiring activity data representing at least one desired activity of the patient to be possible after implanting the implant pair, wherein each of the at least one desired activity has an associated range of motion between the first bone and the second bone;
   calculating a range of motion volume, which represents possible orientations between the first bone and the second bone over three rotational axes, from the implant orientation data, the second implant orientation data and the implant shape data;
   displaying the range of motion volume and the associated range of motion corresponding to each of the at least one desired activity; and
   judging the implant orientation data to be feasible if the associated range of motion corresponding to each of the at least one desired activity lies within the range of motion volume.

2. The method of claim 1, wherein calculating the range of motion volume comprises the steps of:
   calculating a zero joint orientation of an implant joint formed by the first implant part and the second implant part, in which the first bone and the second bone are in a neutral position relative to each other, from the implant orientation data and the second implant orientation data;
   calculating an implant range of motion volume, which represents possible orientations between the first implant part and the second implant part relative to the zero joint orientation over the three rotational axes, from the implant shape data; and
   using the implant range of motion volume as the range of motion volume.

3. The method of claim 1, wherein the at least one desired activity comprises one or more higher priority activities and one or more lower priority activities, and the implant orientation data is judged to be feasible if the associated range of motion corresponding to each of the one or more higher priority activities lies within the range of motion volume.

4. The method of claim 1, wherein the three rotational axes are the axes of flexion-extension rotation, adduction-abduction rotation and internal-external rotation.

5. The method of claim 1, wherein the associated range of motion of each of the at least one desired activity is defined by one or more relative orientations between the first bone and the second bone.

6. The method of claim 1, wherein the implant orientation data is obtained by one of tracking the first implant part and planning the orientation of the first implant part by a computing device.

7. The method of claim 1, wherein displaying comprises displaying a sectional view of the range of motion volume.

8. The method of claim 7, wherein displaying further comprises displaying a sectional view of the associated range of motion corresponding to each of the at least one desired activity in a same sectional plane as the range of motion volume.

9. A data processing method performed by a computer for judging implant orientation data representing an orientation of a first implant part relative to a first bone, the first implant part being part of an implant pair which further comprises a second implant part for a second bone, the implant pair configured to be implanted in a patient, comprising the steps of:
   acquiring the implant orientation data;
   acquiring second implant orientation data representing an orientation of the second implant part relative to the second bone;
   acquiring implant shape data representing a shape of the first implant part and a shape of the second implant part;
   acquiring activity data representing at least one desired activity of the patient to be possible after implanting the implant pair, wherein each of the at least one desired activity has an associated range of motion between the first bone and the second bone;
   transforming the associated range of motion corresponding to each of the at least one desired activity into an implant range of motion which defines a corresponding range of motion between the first implant part and the second implant part, by use of the implant orientation data and the second implant orientation data;
   calculating an implant range of motion volume, which represents possible orientations between the first implant part and the second implant part over three rotational axes, from the implant shape data;
   displaying the implant range of motion volume and the implant range of motion corresponding to each of the at least one desired activity; and judging the implant orientation data to be feasible if the implant range of motion corresponding to each of the at least one desired activity lies within the implant range of motion volume.

10. The method of claim 9, further comprising calculating a zero joint orientation of an implant joint formed by the first implant part and the second implant part, in which the first bone and the second bone are in a neutral position relative to each other, from the implant orientation data and the second implant orientation data, wherein the implant range of motion volume is calculated relative to the zero joint orientation.

11. The method of claim 9, wherein calculating the implant range of motion volume involves finding possible orientations in which the first implant part and the second implant part do not impinge.

12. The method of claim 11, wherein a determination of whether or not the first implant part and the second implant part impinge is made by a collision detection of 3D models of the first implant part and the second implant part.

13. The method of claim 11, wherein a determination of whether or not the first implant part and the second implant part impinge is made by an analytical analysis of the implant shape data.

14. The method of claim 9, wherein the three rotational axes are the axes of flexion-extension rotation, adduction-abduction rotation and internal-external rotation.

15. The method of claim 9, wherein the associated range of motion of each of the at least one desired activity is defined by one or more relative orientations between the first bone and the second bone.

16. The method of claim 9, wherein the implant orientation data is obtained by one of tracking the first implant part and planning the orientation of the first implant part by a computing device.

17. The method of claim 9, further comprising determining one or more of the at least one desired activity for which the associated range of motion or implant range of motion does not lie in the range of motion volume or implant range of motion volume, respectively.

18. The method of claim 9, wherein the at least one desired activity comprises one or more higher priority activities and one or more lower priority activities, and the implant orientation data is judged to be feasible if the associated range of motion or the implant range of motion corresponding to each of the one or more higher priority activities lies within the range of motion volume or the implant range of motion volume, respectively.

19. The method of claim 9, wherein the implant orientation data represents the orientation of the first implant part in two rotational dimensions.

20. A non-transitory computer readable storage medium comprising a computer program which, when running on a computer or when loaded onto a computer, is configured to cause the computer to perform a data processing method for judging implant orientation data representing an orientation of a first implant part relative to a first bone, the first implant part being part of an implant pair which further comprises a second implant part for a second bone, the implant pair configured to be implanted in a patient, comprising the steps of:
acquiring the implant orientation data;
acquiring second implant orientation data representing an orientation of the second implant part relative to the second bone;
acquiring implant shape data representing a shape of the first implant part and a shape of the second implant part;
acquiring activity data representing at least one desired activity of the patient to be possible after implanting the implant pair, wherein each of the at least one desired activity has an associated range of motion between the first bone and the second bone;
calculating a range of motion volume, which represents possible orientations between the first bone and the second bone over three rotational axes, from the implant orientation data, the second implant orientation data and the implant shape data;
displaying the range of motion volume and the associated range of motion corresponding to each of the at least one desired activity; and
judging the implant orientation data to be feasible if the associated range of motion corresponding to each of the at least one desired activity lies within the range of motion volume.

21. A method performed by at least one processor for planning an implant orientation, the method comprising:
receiving implant data comprising characteristics of a fixed implant, characteristics of an adjustable implant, and an orientation of the fixed implant relative to a first bone;
receiving activity data comprising one or more post-operative activities;
identifying, based on the activity data, a required range of motion for each of the one or more post-operative activities;
calculating, based on the implant data, range of motion values for one or more proposed orientations of the adjustable implant relative to a second bone, wherein the range of motion values are associated with one or more possible orientations between the fixed implant and the adjustable implant with respect to each of one or more rotational axes;
determining, based on the range of motion values, whether any of the one or more proposed orientations have range of motion values that encompass the required range of motion for each of the one or more post-operative activities; and
providing, based on said determination, planning information comprising an orientation between the adjustable implant and the second bone.

22. The method of claim 21, wherein each of the one or more post-operative activities has an associated priority level, and further comprising:
responsive to determining that a plurality of the one or more proposed orientations have range of motion values that encompasses the required range of motion of any of the one or more post-operative activities, ranking, based on the associated priority level of each of the one or more post-operative activities, the plurality of the one or more proposed orientations.

23. The method of claim 21, wherein the one or more rotational axes are selected from a group consisting of an axis of flexion-extension rotation, an axis of adduction-abduction rotation, and an axis of internal-external rotation.

* * * * *